United States Patent
Schnapperelle et al.

(10) Patent No.: US 10,532,978 B2
(45) Date of Patent: Jan. 14, 2020

(54) PROCESS FOR THE PRODUCTION OF DIHYDROLIPOIC ACID

(71) Applicant: ALZCHEM TROSTBERG GMBH, Trostberg (DE)

(72) Inventors: Ingo Schnapperelle, Wasserburg (DE); Stephan Winkler, Altenmarkt (DE); Jürgen Sans, Trostberg (DE); Franz Thalhammer, Trostberg (DE)

(73) Assignee: ALZCHEM TROSTBERG GMBH, Trostberg (DE)

( * ) Notice: Subject to any disclaimer, the term of this patent is extended or adjusted under 35 U.S.C. 154(b) by 0 days.

(21) Appl. No.: 16/332,222

(22) PCT Filed: Dec. 22, 2017

(86) PCT No.: PCT/EP2017/084511
§ 371 (c)(1),
(2) Date: Mar. 11, 2019

(87) PCT Pub. No.: WO2018/137874
PCT Pub. Date: Aug. 2, 2018

(65) Prior Publication Data
US 2019/0276396 A1  Sep. 12, 2019

(30) Foreign Application Priority Data
Jan. 28, 2017  (DE) .......... 10 2017 000 811

(51) Int. Cl.
*C07C 319/06* (2006.01)
*C07C 323/52* (2006.01)

(52) U.S. Cl.
CPC .......... *C07C 319/06* (2013.01); *C07C 323/52* (2013.01)

(58) Field of Classification Search
CPC .............. C07C 319/06; C07C 323/52
USPC .......................................... 554/87
See application file for complete search history.

(56) References Cited

U.S. PATENT DOCUMENTS

| | | | |
|---|---|---|---|
| 2,975,198 A | 3/1961 | Reed | |
| 2,980,716 A | 4/1961 | Reed | |
| 5,489,694 A | 2/1996 | Paust et al. | |
| 5,731,448 A * | 3/1998 | Gewald | C07C 51/363 554/85 |
| 2004/0044227 A1 | 3/2004 | Klatt et al. | |
| 2005/0101669 A1 | 5/2005 | Klatt et al. | |

FOREIGN PATENT DOCUMENTS

| | | | |
|---|---|---|---|
| EP | 0763533 | 3/1997 | |
| EP | 0763533 A1 * | 3/1997 | C07C 51/363 |
| WO | 0210151 | 2/2002 | |
| WO | 0244163 | 6/2002 | |

OTHER PUBLICATIONS

Bringmann et al., "A short and productive synthesis of (R)-α-lipoic acid", Zeitschrift für Naturforschung B 54.5 (1999): 655-661.
German Application No. 10 2017 000 811.6, German Search Report dated Jun. 4, 2018, 7 pages.
International Application No. PCT/EP2017/084511, International Search Report and Written Opinion dated Mar. 23, 2018, 14 pages.
Reed et al., "Syntheses of DL-α-Lipoic acid", Journal of the American chemical society 77.2 (1955): 416-419.
Zhang et al., "Synthesis and anticancer evaluation of α-lipoic acid derivatives", Bioorganic & medicinal chemistry letters 20.10 (2010): 3078-3083.

* cited by examiner

*Primary Examiner* — Deborah D Carr
(74) *Attorney, Agent, or Firm* — Kilpatrick Townsend & Stockton LLP

(57) ABSTRACT

The present invention relates to a multi-step process for the production of dihydrolipoic acid, which can particularly be carried out as a one-pot reaction and without isolation of intermediates.

12 Claims, No Drawings

PROCESS FOR THE PRODUCTION OF DIHYDROLIPOIC ACID

The present invention relates to a multi-step process for the production of dihydrolipoic acid, which can particularly be carried out as a one-pot reaction and without isolation of intermediates.

Dihydrolipoic acid ($C_8H_{16}O_2S_2$; 6,8-disulfanyloctanoic acid; CAS no. 462-20-4)

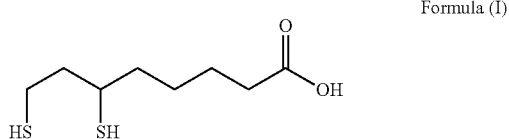 [SMILES: O=C(O)CCCCC(S)CCS]

Formula (I)

is a sulphur-containing carboxylic acid which can be described as an open-chain form of alpha-lipoic acid ($C_8H_{14}O_2S_2$; 5-(1,2-dithiolan-3-yl)-pentanoic acid; CAS no. 1077-28-7) and which, compared with alpha-lipoic acid, has two SH groups instead of an S—S sulphur bridge. Both dihydrolipoic acid and alpha-lipoic acid may be present in two enantiomeric forms (compare R-dihydrolipoic acid (formula Ia) and S-dihydrolipoic acid (formula Ib).

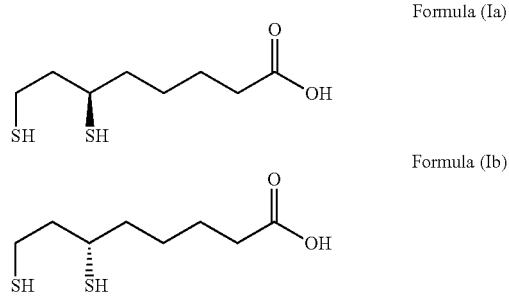

Formula (Ia)

Formula (Ib)

Dihydrolipoic acid is a compound which occurs in the human organism, and which is in physiological equilibrium with alpha-lipoic acid, a substance also known for quite some time as a growth factor in microorganisms, which in addition occurs in low concentrations in higher plants and animals as well. Physiologically speaking, dihydrolipoic acid is the redox partner of alpha-lipoic acid. Due to the discovery of new properties of this natural redox pair, the two natural substances have again increasingly attracted the interest of biology, biochemistry, medicine, nutritional science and technology.

Chemical synthesis of dihydrolipoic acid has been established for a relatively long time, and can in principle be realised by different reaction routes. For example, a process for the production of dihydrolipoic acid in which 6,8-dichlorooctanoic acid ester is reacted with benzyl mercaptan under alkaline conditions in ethanolic solution is described in J. Am. Chem. Soc. 1955, 77, 416-419. Then both benzyl radicals are cleaved off by a reduction with sodium in liquid ammonia, and purification by distillation yields 82% of the product.

Furthermore, a process for the production of dihydrolipoic acid in which 6,8-mesyloxyoctanoic acid ester is reacted with a mixture of sodium sulphide and sulphur and then a reduction by means of sodium borohydride is carried out is described in international patent applications WO 02/10151 A2 and WO 02/44163 A2. The resulting reaction mixture is worked up in a large number of purification steps. It is necessary to distil the dihydrolipoic acid in order to separate off polymers and impurities.

The use of the potassium salt of thioacetic acid to introduce the SH functionality is also described (Z. Naturforschung B. 1999, 54, 655-661). In this case, 6,8-mesyloxyoctanoic acid ester is reacted in dimethyl formamide with potassium thioacetate and then acetyl groups are cleaved off by alkaline hydrolysis. Dihydrolipoic acid is obtained in a yield of 86%.

Furthermore, in U.S. Pat. No. 5,489,694 A, for synthesis of dihydrolipoic acid and alpha-lipoic acid, cyclohexanone is reacted with a vinyl alkyl ether in the presence of a radical starter, the resulting 2-alkoxyethylcyclohexanone is then reacted with a peracid in a Baeyer-Villiger reaction to form a lactone, which subsequently reacts with thiourea and in the presence of hydrobromic acid or hydroiodic acid to form dihydrolipoic acid. The crude dihydrolipoic acid thus obtained is either isolated or oxidised to form alpha-lipoic acid in the presence of an iron (III) catalyst. The crude alpha-lipoic acid is finally distilled in a thin-film evaporator by continuous distillation at 0.2 to 0.02 mbar and 60 to 200° C., and the distillate is crystallised (preferably from diisopropyl ether or a mixture of hexane or ethyl acetate).

The disadvantages of this synthesis route are the low selectivity of the radical addition of cyclohexanone to the vinyl derivative, the occurrence of product mixtures after the Baeyer-Villiger oxidation, and again the necessity of purifying the thermally labile products by distillation.

The object of the present invention is to provide a novel process for the production of dihydrolipoic acid which can be applied in a simple manner even on a large scale, largely represses the reaction of by-products and permits a high space-time yield.

These objects are achieved by a process according to claim 1. Preferred embodiments of the invention are set forth in the dependent claims, and can be combined as desired.

Thus, according to a first embodiment the subject of the present invention is a multi-step process for producing dihydrolipoic acid in which a) in a first process stage, an ester of 6,8-dichlorooctanoic acid according to general formula (II) is caused to react with a mixture comprising sodium sulphide and sulphur, wherein formula (II) is

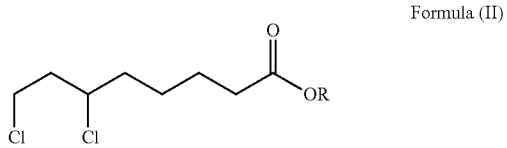

Formula (II)

wherein for the radical R:
R=C1 to C6 alkyl,
and wherein the reaction is carried out in an alcoholic solvent mixture at a temperature in the range from 80° C. to 130° C. and a pressure in the range from 0.12 MPa to 0.60 MPa, b) in a second process stage, the reaction mixture obtained from the first process stage is subjected to a reduction, and c) in a third process stage, the reaction mixture resulting from the second process stage is set to a pH value in the range from pH 1.5 to <7 by means of a mineral acid and dihydrolipoic acid is released.

It is essential to the invention that the process is carried out such that the first process stage is carried out in an alcoholic solvent mixture at a temperature in the range from 80° C. to 130° C. and at a pressure of 0.12 MPa to 0.60 MPa. Preferably the process is carried out such that the first process stage is carried out in an alcoholic solvent mixture at a temperature in the range from 100° C. to 130° C. and at a pressure of 0.12 MPa to 0.60 MPa, most preferably at a temperature in the range from 110° C. to 130° C. and at a pressure of 0.25 MPa to 0.50 MPa. Unless otherwise indicated, the pressure values quoted herein are absolute pressure values.

Surprisingly, it has been shown that with such reaction conditions the proportion of polymeric compounds which inevitably result as a by-product of the synthesis can be significantly lowered. Thus by applying the process according to the invention a significantly higher space-time yield can be realised in relation to the reagents used. In addition, it was found, completely surprisingly, that no additional by-products are produced under the set reaction conditions. The formation of the polymeric compounds is thus repressed entirely in favour of the desired product. These facts, taken together, were completely surprising and in no way predictable.

In conjunction with the present invention, C1 to C6 alkyl is to be understood to mean a linear or branched alkyl radical with a number of up to 6 carbon atoms, which corresponds in particular to the general formula $C_nH_{2n+1}$, wherein n=1 to 6. In this case, provision is preferably made for C1 to C6 alkyl to mean methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl or 1-ethylpropyl or n-hexyl.

It should be emphasised at this point that the process according to the invention can be used both for the production of racemic dihydrolipoic acid and for the production of enantiomerically pure R-dihydrolipoic acid or enantiomerically pure S-dihydrolipoic acid. For the production of these substances, then the dichlorooctanoic acid ester serving as reagent for the process has to be used in the corresponding form. Thus for example according to the present invention racemic dihydrolipoic acid can be produced from racemic dichlorooctanoic acid esters, R-dihydrolipoic acid from S-dichlorooctanoic acid esters and S-dihydrolipoic acid from R-dichlorooctanoic acid esters.

According to a preferred embodiment of the present invention, thus also a process in which racemic 6,8-dichlorooctanoic acid ethyl esters, enantiomerically pure R-6,8-dichlorooctanoic acid ethyl esters, enantiomerically pure S-6,8-dichlorooctanoic acid ethyl esters or any mixtures thereof are used as esters of dichlorooctanoic acid according to formula (II) is the subject of the present invention.

Regardless of this, thus a multi-step process for the production of R-dihydrolipoic acid or S-dihydrolipoic acid or a mixture thereof is also the subject of the present invention, in which a) in a first process stage an ester of 6,8-dichlorooctanoic acid according to general formula (IIa) (S-dichlorooctanoic acid ester) or of the general formula (IIb) (R-dichlorooctanoic acid ester) or a mixture thereof is caused to react with a mixture comprising sodium sulphide and sulphur, wherein formulae (IIa) and (IIb) are:

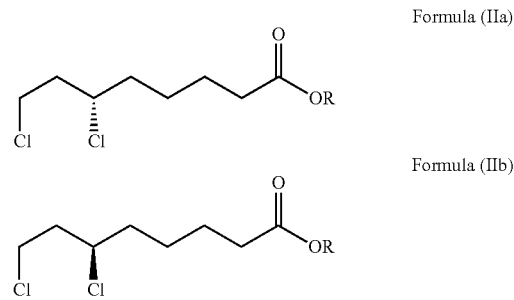

wherein for the radical R:
R=C1 to C6 alkyl,
and wherein the reaction of the first process stage is carried out in an alcoholic solvent mixture at a temperature in the range from 80° C. to 130° C. and a pressure in the range from 0.12 MPa to 0.60 MPa, b) in a second process stage, the reaction mixture obtained from the first process stage is subjected to a reduction, and c) in a third process stage, the reaction mixture resulting from the second process stage is set to a pH value in the range from pH 1.5 to <7 by means of a mineral acid and the R-dihydrolipoic acid or S-dihydrolipoic acid or a mixture thereof is released.

Preferably the process is carried out such that the first process stage is carried out in an alcoholic solvent mixture at a temperature in the range from 100° C. to 130° C. and at a pressure of 0.12 MPa to 0.60 MPa, most preferably at a temperature in the range from 110° C. to 130° C. and at a pressure of 0.25 MPa to 0.50 MPa.

According to a preferred embodiment of the process, in particular a C1 to C3 alkylester of 6,8-dichlorooctanoic acid, in particular of racemic 6,8-dichlorooctanoic acid, of R-dichlorooctanoic acid or of S-dichlorooctanoic acid, can be used. Thus the radical R in formula (II), (IIa) or (IIb) stands in particular for R=methyl, ethyl or n-propyl. These radicals can be cleaved off particularly readily under comparatively mild reaction conditions in order to release the desired product.

The sodium sulphide used according to the invention is $Na_2S$.

The alcoholic solvent mixture used according to the invention is preferably a mixture of one or more alcohols and water. An alcoholic solution mixture comprising one or more alcohols from the group consisting of methanol, ethanol, propanol and/or isopropanol and also water is preferred. It is however also possible to use only one alcohol or a mixture of two or more alcohols as alcoholic solvent mixture, in particular a mixture comprising two or more alcohols selected from the group consisting of methanol, ethanol, propanol and isopropanol.

The proportion of alcohol in the alcoholic solvent mixture is preferably 5 wt. % to 100 wt. %, more preferably at least 10 wt. % and even more preferably at least 15 wt. % and up to 80 wt. %, preferably up to 60 wt. %, even more preferably up to 50 wt. %. The proportion of water in the alcoholic solvent mixture is preferably 5 wt. % to 95 wt. % and in particular at least 10 wt. %, more preferably at least 20 wt. %, even more preferably at least 50 wt. % and up to 90 wt. % and in particular up to 80 wt. %.

More preferably, the alcoholic solvent mixture is a mixture of ethanol and water, most preferably a mixture comprising 20 wt. % to 30 wt. % ethanol and 70 wt. % to 80 wt. % water.

According to the present invention, the process is carried out such that in the second process stage the reaction mixture obtained from the first process stage is subjected to a reduction. In this case, a large number of reduction reactions can be used. In the context of a more preferred embodiment of the invention, provision is made for the reduction of the second stage to take place by addition of a solution of sodium borohydride in a lye. More preferably, in such case a dilute or concentrated lye, preferably a dilute or concentrated sodium hydroxide solution, potassium hydroxide solution or a solution comprising sodium carbonate, potassium carbonate can be used as the lye. At the same time or independently thereof, the reduction in the second stage can more preferably be carried out at a temperature in the range from 60° C. to 85° C. and/or at normal pressure.

The reaction conditions for the reduction which are thus set can be classified as mild, and promote the desired course of the reaction particularly well. In particular, furthermore fewer secondary reactions are observed as a result. In particular, the tendency of the resulting intermediates to polymerise which is particularly advantageously repressed by the first stage is not promoted either, so the degree of polymerisation of the first stage can be maintained.

According to a more preferred embodiment of the process, provision may also be made for the ester of 6,8-dichlorooctanoic acid and sodium sulphide in the first stage to be caused to react in a molar ratio of ester of 6,8-dichlorooctanoic acid to sodium sulphide in the range from 1:1 to 1:2, in particular in the range from 1:1 to 1:1.5, and more preferably in the range from 1:1.1 to 1:1.3. In particular, a small molar excess of sodium sulphide used has led to good results in relation to the ester of 6,8-dichlorooctanoic acid which is used.

In addition, furthermore preferably in the first process stage a mixture of sodium sulphide and sulphur can be used in which the molar ratio of sodium sulphide to sulphur lies in the range from 0.8:1 to 2:1, preferably in the range from 0.8:1 to 1.5:1, and more preferably in the range from 0.8:1 to 1.2:1.

In a further preferred embodiment, in the first process stage a mixture of sodium sulphide and sulphur is used, in which the molar ratio of sodium sulphide to sulphur lies in the range from 1:1 to 2:1, preferably in the range from 1:1 to 1.6:1, and more preferably in the range from 1.2:1 to 1.5:1.

At the same time or independently thereof, in so doing more preferably provision may be made for the sulphur together with the 6,8-dichlorooctanoic acid ester, in particular the racemic 6,8-dichlorooctanoic acid ester, the R-dichlorooctanoic acid ester or the S-dichlorooctanoic acid ester, to be placed in the alcoholic solvent mixture, and for sodium sulphide, in particular sodium sulphide solution, to be added. Furthermore, it is preferred to place the sulphur together with the 6,8-dichlorooctanoic acid ester, in particular a racemic 6,8-dichlorooctanoic acid ester, an R-dichlorooctanoic acid ester or an S-dichlorooctanoic acid ester, in an alcohol or alcohol mixture and then to add sodium sulphide, in particular an aqueous sodium sulphide solution.

In the third process stage in step c), the pH value is preferably set according to the invention to a range from pH 1.5 to 5, more preferably to pH 1.5 to 4, and most preferably to pH 1.5 to 3.

In a particular embodiment of the invention, the production according to the invention of the dihydrolipoic acid takes place in a one-pot reaction, in particular without isolation or purification of the intermediates from the first or the second process stage. Thus the process can be carried out particularly efficiently. It is particularly surprising in this case that even with knowledge of the known reaction routes of sulphur compounds even in the performance of the reaction as a one-pot reaction, no by-products of note are formed. This fact is particularly surprising and, without being bound by the theory, can be attributed to the reaction conditions set in the first process stage.

Thus a process for the production of dihydrolipoic acid of the type described herewith is also a subject of the present invention, in that the process is carried out as a one-pot reaction and/or without isolation of an intermediate stage.

In this process, in particular in the first process stage, more preferably an alcohol selected from the group consisting of methanol, ethanol, propanol, isopropanol or mixtures thereof or mixtures of these alcohols with water can be used as the alcoholic solvent mixture. These alcohols which are used may be used as absolute solvents or as technical solvents with a proportion of water.

Lastly, non-restrictively, a dilute or concentrated mineral acid, preferably a dilute or concentrated hydrochloric acid, nitric acid or sulphuric acid, can be used as the mineral acid in the third process stage.

In a further advantageous embodiment of the process according to the invention, in step b) the alcohol used in the first process step and contained in the alcoholic solution mixture is removed at least in part, advantageously virtually completely. In particular, at least 50 wt. %, more preferably at least 80 wt. %, even more preferably at least 90 wt. % and most preferably at least 95 wt. % and up to 100 wt. %, more preferably up to 99 wt. % and even more preferably up to 98 wt. %, of the alcohol used in the first process step is removed in step b). Advantageously, in this case first of all a first reduction step is carried out, then the alcohol is removed and then a second reduction step is performed.

Furthermore preferably, according to the invention after step b) and prior to step c) a solvent for the desired product dihydrolipoic acid, in particular an ether, and most preferably methyl tert-butyl ether (MTBE), is added.

The addition of this solvent for the desired product dihydrolipoic acid and in particular the addition of an ether preferably takes place prior to addition of a mineral acid.

In summary, it should be recorded that the present invention makes it possible to obtain dihydrolipoic acid economically and on a large scale, which can be converted into alpha-lipoic acid or physiologically compatible derivatives with an efficiency not known hitherto.

The following examples are intended to illustrate the advantages of the process according to the invention for the production of dihydrolipoic acid.

EXAMPLES

Example 1

123.0 g (500 mmol) racemic 6,8-dichloroethyl caprylate and 14.4 g (450 mmol, 0.9 equiv.) sulphur in 123.0 g ethanol were placed in a 1000 ml autoclave with stirrer, metering pump, pressure and internal temperature measurement and also jacket heating. The autoclave was closed and heated with stirring to an internal temperature of 110° C. At this temperature, 412.5 g of an aqueous sodium sulphide solution (12.3 wt. % $Na_2S$ in water) comprising 50.7 g $Na_2S$ (650 mmol, 1.3 equiv.) was metered in uniformly over a period of 60 min. In so doing, the pressure rose from an initial 0.33 MPa to 0.43 MPa. The reaction mixture was stirred for another 120 min. at 110° C., then cooled to 50° C. and transferred into a 2000 ml four-neck flask with stirrer, metering pump, internal thermometer, reflux condenser and oil bath heating. 94.6 g of a solution of sodium borohydride (12 wt. %) in sodium hydroxide solution (40 wt. %) comprising 11.4 g $NaBH_4$ (300 mmol, 0.60 equiv.) was added uniformly dropwise within 30 min. at 70° C. The ethanol contained was distilled off to the greatest possible extent (up to 98° C. overhead temperature) from the reaction mixture over a period of 60 min. and the contents were then cooled to room temperature.

The next day, a further 47.3 g of a solution of sodium borohydride (12 wt. %) in sodium hydroxide solution (40 wt. %) comprising 5.68 g $NaBH_4$ (150 mmol, 0.3 equiv.) was added to the reaction mixture at 70° C. over a period of 30 min. Once addition had taken place, the mixture was heated to boiling and stirred further for 30 min. at this temperature. After cooling, 250 ml methyl tert-butyl ether (MTBE) was added and the batch was acidified to a pH value of 1.5 to 2.0 by adding 250.6 g (2200 mmol) hydrochloric acid (32 wt. %) dropwise. The organic phase was separated off in a separating funnel, the aqueous phase was extracted with 50 ml MTBE and the combined organic phases were dried over magnesium sulphate. The drying agent was filtered off and the filtrate was completely reduced in volume on a rotary evaporator. 101.1 g of a yellow liquid was obtained, with a content of 85.9 wt. % dihydrolipoic acid and a polymer content of 11.4 wt. % (corresponds to a yield of 83.4% of theory).

Example 2

Comparative Example, not in Accordance with the Invention 123.0 g (500 mmol) racemic 6,8-dichloroethyl caprylate and 14.4 g (450 mmol, 0.9 equiv.) sulphur in 123.0 g ethanol were placed in a 2000 ml four-neck flask with stirrer, metering pump, internal thermometer and reflux condenser, and were heated to an internal temperature of 75° C. at normal pressure. At this temperature, 412.5 g of an aqueous sodium sulphide solution (12.3 wt. % $Na_2S$ in water) comprising 50.7 g $Na_2S$ (650 mmol, 1.3 equiv.) was metered in uniformly over a period of 60 min., and the reaction mixture was then stirred for another 120 min at 75° C. The content of the reaction was cooled to a temperature of 70° C. and then 94.6 g of a solution of sodium borohydride (12 wt. %) in sodium hydroxide solution (40 wt. %) comprising 11.4 g $NaBH_4$ (300 mmol, 0.60 equiv.) was added uniformly dropwise within 30 min. The ethanol contained was distilled off to the greatest possible extent (up to 98° C. overhead temperature) from the reaction mixture over a period of 60 min. Thereafter, a further 47.3 g of a solution of sodium borohydride (12 wt. %) in sodium hydroxide solution (40 wt. %) comprising 5.68 g $NaBH_4$ (150 mmol, 0.3 equiv.) was added dropwise over a period of 30 min. at 70° C. Once addition had taken place, the mixture was heated to boiling, stirred further for 30 min. at this temperature and then cooled to room temperature.

The next day, 250 ml MTBE was added to the reaction mixture and the batch was acidified to a pH value of 1.5 to 2.0 by adding 250.9 g (2202 mmol) hydrochloric acid (32 wt. %) dropwise. The organic phase was separated off in a separating funnel, the aqueous phase was extracted with 50 ml MTBE and the combined organic phases were dried over magnesium sulphate. The drying agent was filtered off and the filtrate was completely reduced in volume on a rotary evaporator. 99.9 g of a yellow liquid was obtained, with a content of 75.6 wt. % dihydrolipoic acid and a polymer content of 19.8 wt. % (corresponds to a yield of 72.5% of theory).

Example 3

123.0 g (500 mmol) racemic 6,8-dichloroethyl caprylate and 16.0 g (500 mmol, 1.0 equiv.) sulphur in 123.0 g ethanol were placed in a 1000 ml autoclave with stirrer, metering pump, pressure and internal temperature measurement and also jacket heating. The autoclave was closed and heated with stirring to an internal temperature of 110° C. At this temperature, 421.0 g of an aqueous sodium sulphide solution (12.3 wt. %) comprising 51.8 g $Na_2S$ (663 mmol, 1.33 equiv.) was metered in uniformly over a period of 60 min. In so doing, the pressure rose from an initial 0.29 MPa to 0.45 MPa. The reaction mixture was stirred for another 120 min. at 110° C., then cooled to 50° C. and transferred into a 2000 ml four-neck flask with stirrer, metering pump, internal thermometer, reflux condenser and oil bath heating. 99.3 g of a solution of sodium borohydride (12 wt. %) in sodium hydroxide solution (40 wt. %) comprising 11.9 g $NaBH_4$ (315 mmol, 0.63 equiv.) was added uniformly dropwise within 30 min. at 70° C. The ethanol contained was distilled off to the greatest possible extent (up to 98° C. overhead temperature) from the reaction mixture over a period of 60 min. and the contents were then cooled to room temperature.

The next day, a further 49.7 g of a solution of sodium borohydride (12 wt. %) in sodium hydroxide solution (40 wt. %) comprising 5.96 g $NaBH_4$ (158 mmol, 0.32 equiv.) was added to the reaction mixture at 70° C. over a period of 30 min. Once addition had taken place, the mixture was heated to boiling and stirred further for 30 min. at this temperature. After cooling, 250 ml MTBE was added and the batch was acidified to a pH value of 1.5 to 2.0 by adding 263.4 g (2312 mmol) hydrochloric acid (32 wt. %) dropwise. The organic phase was separated off in a separating funnel, the aqueous phase was extracted with 50 ml MTBE and the combined organic phases were dried over magnesium sulphate. The drying agent was filtered off and the filtrate was completely reduced in volume on a rotary evaporator. 102.3 g of a yellow liquid was obtained, with a content of 89.8 wt. % dihydrolipoic acid and a polymer content of 9.8 wt. % (corresponds to a yield of 88.2% of theory).

Example 4

600 kg (2.48 kmol) racemic 6,8-dichloroethyl caprylate and 78 kg (2.43 kmol, 0.98 equiv.) sulphur in 576 kg ethanol were placed in a 6 m³ reactor with stirrer, metering pump, pressure and internal temperature measurement and also jacket heating. At an internal temperature of 110° C. and a pressure of 0.35 MPa, 2062 kg of an aqueous sodium sulphide solution (12.3 wt. %) comprising 253.6 kg $Na_2S$ (3.24 kmol, 1.31 equiv.) was metered in uniformly with stirring over a period of 85 min. The reaction mixture was stirred for another 120 min at 110° C. Then 508 g of a solution of sodium borohydride (12 wt. %) in sodium hydroxide solution (40 wt. %) comprising 61.0 kg $NaBH_4$ (1.61 kmol, 0.65 equiv.) was metered in uniformly within 90 min. at 70° C. The ethanol contained was distilled off from the reaction mixture to the greatest possible extent, and thereupon a further 253 kg of a solution of sodium borohydride (12 wt. %) in sodium hydroxide solution (40 wt. %) comprising 30.4 kg $NaBH_4$ (0.80 kmol, 0.32 equiv.) added over a period of 60 min. at 70° C. Once addition had taken place, the mixture was heated to boiling and stirred further for 30 min. at this temperature. After cooling, 540 kg MTBE was added and the batch was acidified to a pH value of 2.6 to 3.0 by adding 1454 kg (12.3 kmol) hydrochloric acid (31 wt. %). The organic phase was separated off and the organic solvent was distilled off completely without a vacuum. 506 kg of a yellow liquid was obtained, with a content of 94.0 wt. % dihydrolipoic acid and a polymer content of 5.6 wt. % (corresponds to a yield of 91.8% of theory).

Example 5

123.0 g (500 mmol) racemic 6,8-dichloroethyl caprylate and 14.4 g (450 mmol, 0.9 equiv.) sulphur in 123.0 g ethanol were placed in a 1000 ml autoclave with stirrer, metering pump, pressure and internal temperature measurement and also jacket heating. The autoclave was closed and heated with stirring to an internal temperature of 100° C. At this temperature, 412.5 g of an aqueous sodium sulphide solution (12.3 wt. % $Na_2S$ in water) comprising 50.7 g $Na_2S$ (650 mmol, 1.3 equiv.) was metered in uniformly over a period of 60 min. In so doing, the pressure rose from an initial 0.23 MPa to 0.38 MPa. The reaction mixture was stirred for another 120 min. at 100° C., then cooled to 50° C. and transferred into a 2000 ml four-neck flask with stirrer, metering pump, internal thermometer, reflux condenser and oil bath heating. 94.6 g of a solution of sodium borohydride (12 wt. %) in sodium hydroxide solution (40 wt. %) comprising 11.4 g $NaBH_4$ (300 mmol, 0.60 equiv.) was added uniformly dropwise within 30 min. at 70° C. The ethanol contained was distilled off to the greatest possible extent (up to 98° C. overhead temperature) from the reaction mixture over a period of 60 min. and the contents were then cooled to room temperature.

The next day, a further 47.3 g of a solution of sodium borohydride (12 wt. %) in sodium hydroxide solution (40 wt. %) comprising 5.68 g $NaBH_4$ (150 mmol, 0.3 equiv.) was added to the reaction mixture at 70° C. over a period of 30 min. Once addition had taken place, the mixture was heated to boiling and stirred further for 30 min. at this temperature. After cooling, 250 ml methyl tert-butyl ether (MTBE) was added and the batch was acidified to a pH value of 1.5 to 2.0 by adding 251.5 g (2207 mmol) hydrochloric acid (32 wt. %) dropwise. The organic phase was separated off in a separating funnel, the aqueous phase was extracted with 50 ml MTBE and the combined organic phases were dried over magnesium sulphate. The drying agent was filtered off and the filtrate was completely reduced in volume on a rotary evaporator. 99.4 g of a yellow liquid was obtained, with a content of 83.2 wt. % dihydrolipoic acid and a polymer content of 12.0 wt. % (corresponds to a yield of 79.4% of theory).

Example 6

123.0 g (500 mmol) racemic 6,8-dichloroethyl caprylate and 14.4 g (450 mmol, 0.9 equiv.) sulphur in 123.0 g ethanol were placed in a 1000 ml autoclave with stirrer, metering pump, pressure and internal temperature measurement and also jacket heating. The autoclave was closed and heated with stirring to an internal temperature of 120° C. At this temperature, 412.5 g of an aqueous sodium sulphide solution (12.3 wt. % $Na_2S$ in water) comprising 50.7 g $Na_2S$ (650 mmol, 1.3 equiv.) was metered in uniformly over a period of 60 min. In so doing, the pressure rose from an initial 0.35 MPa to 0.46 MPa. The reaction mixture was stirred for another 120 min. at 120° C., then cooled to 50° C. and transferred into a 2000 ml four-neck flask with stirrer, metering pump, internal thermometer, reflux condenser and oil bath heating. 94.6 g of a solution of sodium borohydride (12 wt. %) in sodium hydroxide solution (40 wt. %) comprising 11.4 g $NaBH_4$ (300 mmol, 0.60 equiv.) was added uniformly dropwise within 30 min. at 70° C. The ethanol contained was distilled off to the greatest possible extent (up to 98° C. overhead temperature) from the reaction mixture over a period of 60 min. and the contents were then cooled to room temperature.

The next day, a further 47.3 g of a solution of sodium borohydride (12 wt. %) in sodium hydroxide solution (40 wt. %) comprising 5.68 g $NaBH_4$ (150 mmol, 0.3 equiv.) was added to the reaction mixture at 70° C. over a period of 30 min. Once addition had taken place, the mixture was heated to boiling and stirred further for 30 min. at this temperature. After cooling, 250 ml methyl tert-butyl ether (MTBE) was added and the batch was acidified to a pH value of 1.5 to 2.0 by adding 251.3 g (2206 mmol) hydrochloric acid (32 wt. %) dropwise. The organic phase was separated off in a separating funnel, the aqueous phase was extracted with 50 ml MTBE and the combined organic phases were dried over magnesium sulphate. The drying agent was filtered off and the filtrate was completely reduced in volume on a rotary evaporator. 100.6 g of a yellow liquid was obtained, with a content of 87.5 wt. % dihydrolipoic acid and a polymer content of 11.1 wt. % (corresponds to a yield of 84.5% of theory).

The invention claimed is:
1. A multi-step process for producing dihydrolipoic acid, comprising:
   a) in a first process stage, an ester of 6,8-dichlorooctanoic acid according to general formula (II) is caused to react with a mixture comprising sodium sulphide and sulphur, wherein formula (II) is

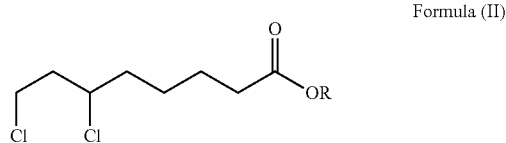

Formula (II)

wherein R is C1 to C6 alkyl,
   wherein the reaction is carried out in an alcoholic solvent mixture at a temperature in a range from 80° C. to 130° C. and a pressure in a range from 0.12 MPa a to 0.60 MPa;
   b) in a second process stage, the reaction mixture obtained from the first process stage is subjected to a reduction; and
   c) in a third process stage, the reaction mixture resulting from the second process stage is set to a pH value in a range from pH 1.5 to <7 by means of a mineral acid and dihydrolipoic acid is released.

2. The multi-step process according to claim 1, wherein R is methyl, ethyl, or n-propyl.

3. The multi-step process according to claim 1, wherein the reduction in the second process stage takes place by addition of a solution of sodium borohydride in a lye.

4. The multi-step process according to claim 3, wherein the lye is a dilute or concentrated lye.

5. The multi-step process according to claim 4, wherein the dilute or concentrated lye comprises a sodium hydroxide solution, a potassium hydroxide solution, a sodium carbonate solution, a potassium carbonate solution, or mixtures thereof.

6. The multi-step process according to claim 1, wherein the reduction in the second process stage is carried out at a temperature in a range from 60° C. to 85° C. and/or at normal pressure.

7. The multi-step process according to claim 1, wherein the multi-step process is carried out as a one-pot reaction and/or without isolation of an intermediate stage.

8. The multi-step process according to claim 1, wherein in the first process stage the ester of 6,8-dichlorooctanoic acid and sodium sulphide are caused to react in a molar ratio of ester of 6,8-dichlorooctanoic acid to sodium sulphide in a range from 1:1 to 1:2.

9. The multi-step process according to claim 1, wherein the mixture comprising sodium sulphide and sulphur of the first process stage contains sodium sulphide and sulphur in a molar ratio of sodium sulphide to sulphur in a range from 0.8:1 to 2:1.

10. The multi-step process according to claim 1, wherein an alcohol selected from the group consisting of methanol, ethanol, propanol, isopropanol or mixtures thereof or mixtures of these alcohols with water is used as the alcoholic solvent mixture.

11. The multi-step process according to claim 1, wherein the mineral acid comprises a dilute or concentrated mineral acid.

12. The multi-step process according to claim 11, wherein the dilute or concentrated mineral acid comprises hydrochloric acid, nitric acid, or sulphuric acid.

* * * * *